United States Patent
Restle et al.

(10) Patent No.: US 6,338,842 B1
(45) Date of Patent: Jan. 15, 2002

(54) COSMETIC COMPOSITION COMPRISING AN ANIONIC SURFACTANT, AN AMPHOTERIC SURFACTANT, A POLYOLEFIN, A CATIONIC POLYMER AND A SALT OR AN ALCOHOL WHICH IS WATER-SOLUBLE, USE AND PROCESS

(75) Inventors: Serge Restle, Saint-Prix (FR); Nathalie Garnier, Springfield, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/496,916

(22) Filed: Feb. 3, 2000

(30) Foreign Application Priority Data

Feb. 3, 1999 (FR) .............................................. 99 01239

(51) Int. Cl.$^7$ ............................................ A61K 7/06
(52) U.S. Cl. .................. 424/70.1; 424/401; 424/70.11; 424/70.19; 424/70.21; 424/70.22; 510/130
(58) Field of Search ........................... 424/40, 1, 70.1, 424/70.11, 70.19, 70.21, 70.22

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/22 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/567.6 |
| 2,528,378 A | 10/1950 | Mannheimer | 260/309.6 |
| 2,781,354 A | 2/1957 | Mannheimer | 260/309.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,589,578 A | 6/1971 | Kamphausen | 226/40 |
| 3,874,870 A | 4/1975 | Green et al. | 71/67 |
| 3,929,990 A | 12/1975 | Green et al. | 424/78 |
| 3,966,904 A | 6/1976 | Green et al. | 424/78 |
| 4,001,432 A | 1/1977 | Green et al. | 424/78 |
| 4,005,193 A | 1/1977 | Green et al. | 424/168 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/597.6 P |
| 4,027,020 A | 5/1977 | Green et al. | 424/248.56 |
| 4,031,307 A | 6/1977 | DeMartino et al. | 536/114 |
| 4,131,576 A | 12/1978 | Iovine et al. | 260/17.46 C |
| 4,832,872 A | * 5/1989 | Scandel | 252/547 |
| 5,853,708 A | * 12/1998 | Cauwet et al. | 424/70.22 |
| 6,028,041 A | * 2/2000 | Decoster et al. | 510/119 |

FOREIGN PATENT DOCUMENTS

| | | |
|---|---|---|
| EP | 0 122 324 | 10/1984 |
| EP | 0 337 354 | 10/1989 |
| EP | 0 413 417 | 2/1991 |
| EP | 0 422 862 | 4/1991 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 1/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| WO | WO 97/35542 | 10/1997 |
| WO | WO 97/35549 | 10/1997 |

OTHER PUBLICATIONS

English language Derwent Abstract of FR 1 583 363.
English language Derwent Abstract of FR 2 077 143.
English language Derwent Abstract of FR 2 080 759.
English language abstract of FR 2 162 025.
English language Derwent Abstract of FR 2 190 406.
English language Derwent Abstract of FR 2 252 840.
English language Derwent Abstract of FR 2 270 846.
English language Derwent Abstract of FR 2 280 361.
English language abstract of FR 2 316 271.
English language Derwent Abstract of FR 2 320 330.
English language Derwent Abstract of FR 2 336 434.
English language abstract of FR 2 368 508.
English language Derwent Abstract of FR 2 383 660.
English language abstract of FR 2 393 573.
English language abstract of FR 2 413 907.
English language abstract of FR 2 470 596.
English language abstract of FR 2 505 348.
English language abstract of FR 2 519 863.
English language abstract of FR 2 542 997.
English language Derwent Abstract of FR 2 598 611.

* cited by examiner

Primary Examiner—Jose' G. Dees
Assistant Examiner—Konata M. George
(74) Attorney, Agent, or Firm—Finnegan, Henderson, Farabow, Garrett & Dunner, L.L.P

(57) ABSTRACT

The invention relates to novel detergent and conditioning compositions having at least one anionic surfactant, at least one amphoteric surfactant, at least one oil of polyolefin type, at least one cationic polymer and at least one water-soluble salt or alcohol; wherein the anionic surfactant/amphoteric surfactant weight ratio being less than or equal to 3; and to application of the compositions to clean and care for the hair or the skin.

44 Claims, No Drawings

COSMETIC COMPOSITION COMPRISING AN ANIONIC SURFACTANT, AN AMPHOTERIC SURFACTANT, A POLYOLEFIN, A CATIONIC POLYMER AND A SALT OR AN ALCOHOL WHICH IS WATER-SOLUBLE, USE AND PROCESS

The present invention relates to novel cosmetic compositions with improved properties, intended simultaneously for cleansing and conditioning keratin substances such as the hair, and comprising, in a cosmetically acceptable aqueous support, at least one anionic surfactant, at least one amphoteric surfactant and at least one oil of polyolefin type, at least one cationic polymer and at least one salt or one alcohol which is water-soluble, the anionic surfactant/amphoteric surfactant weight ratio being less than or equal to 3. The invention also relates to the use of the compositions in the abovementioned cosmetic application.

It is common practice to use detergent compositions (such as shampoos) based essentially on conventional surfactants of anionic, nonionic and/or especially amphoteric type, but, more particularly, of anionic type, for cleansing and/or washing keratin substances, such as the hair. These compositions are applied to wet hair and the lather generated by massaging or friction with the hands allows, after rinsing with water, the removal of the various types of soiling initially present on the hair or the skin. Admittedly, these base compositions have good washing power, but the intrinsic cosmetic properties associated therewith are, nevertheless, fairly poor, especially on account of the fact that the relatively aggressive nature of such a cleansing treatment can lead in the long run to more or less pronounced damage to hair fibers, associated, in particular, with the gradual removal of the lipids or proteins contained in or at the surface of these fibers.

Thus, to improve the cosmetic properties of the above detergent compositions, and, more particularly, of those which are intended to be applied to sensitized hair (i.e., hair which has been damaged or embrittled, in particular, under the chemical action of atmospheric agents and/or of hair treatments such as permanent-waving, dyeing or bleaching operations), it is now common practice to introduce into these compositions additional cosmetic agents known as conditioners, intended mainly to repair or limit the harmful or undesirable effects induced by the various treatments or aggressions to which hair fibers are subjected more or less repeatedly. Needless to say, these conditioners can also improve the cosmetic behavior of natural hair.

With this aim, it has already been proposed to use insoluble conditioners. These insoluble compounds have the drawback of being difficult to keep in uniform dispersion in the medium. To keep them in suspension, it has already been proposed to use derivatives of long-chain esters or ethers (pearlescent agents) or polysaccharides, such as xanthan gum (gelling agents). However, pearlescent agents have crystallization problems, occasionally entailing a change (increase) in the viscosity of the compositions over time; gelling agents also have drawbacks, namely, first, it is difficult to develop a lather with detergent compositions containing polysaccharides (poor starting of lathering) and, second, the compositions do not have a smooth texture and flow in blobs, a feature that users do not particularly appreciate. Furthermore, these various suspending agents do not give transparent or clear compositions.

One aim of the present invention is to propose compositions which do not have the drawbacks of the compositions mentioned above. Conditioners of polyolefin type must also be conveyed onto treated keratin substances to give them, depending on the application, softness, sheen and disentangling properties without giving rise to a greasy nature.

Thus, after considerable research conducted in this matter, the inventors have now found that by using a specific washing base, at least one oil or specific polyolefin type, at least one cationic polymer and at least one water-soluble salt or one water-soluble mono- or polyvalent alcohol, it is possible to obtain stable and transparent detergent compositions having excellent cosmetic properties, especially in terms of the disentangling and smoothing-out of treated hair, and having good properties of use, such as good intrinsic washing power and good foaming power. The industrial implementation is extremely easy and the cosmetic properties of the shampoos are excellent. The compositions obtained are stable during storage, without requiring the addition of an agent for dispersing and/or suspending the oil according to the invention. In the absence of additional insoluble compounds, the compositions obtained are also transparent. They can contain large amounts of oil of polyolefin type while at the same time retaining good transparency and having good cosmetic properties. The compositions according to the invention give the hair, after rinsing, a noteworthy treating effect, manifested, in particular, by an ease of disentangling, as well as smoothness, softness and suppleness without any greasy sensation.

One subject of the present invention is novel detergent and conditioning cosmetic compositions comprising, in a cosmetically acceptable aqueous medium, (A) a washing base comprising at least one anionic surfactant, at least one amphoteric surfactant, (B) at least one oil of polyolefin type with a molecular weight of less than 450, (C) at least one cationic polymer, (D) at least one water-soluble salt and/or at least one mono- or polyhydroxylated water-soluble alcohol, the anionic surfactant/amphoteric surfactant weight ratio being less than or equal to 3. A subject of the invention is also the cosmetic use of the above compositions for cleansing and/or removing make-up from and/or conditioning keratin substances such as the hair and the skin, and a process for washing and conditioning keratin substances by applying the above compositions.

Additional features and advantages of the invention are set forth in the description that follows, and, in part, will be apparent from the description or may be learned from practice of the invention. Both the foregoing general description and the following detailed description of the invention are exemplary and explanatory only and are not restrictive of the claimed invention.

A-Washing Base:

The washing base comprises one or more anionic surfactants and one or more amphoteric surfactants.

(i) Anionic surfactant(s):

In the context of the present invention, their nature is not a genuinely critical feature. Thus, examples of anionic surfactants that can be used, alone or as mixtures, in the context of the present invention, include, in particular, (non-limiting list) of salts (in particular, alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds, preferably containing from 12 to 20 carbon atoms, and the aryl radical preferably denoting a phenyl or benzyl group. Among the anionic surfactants that can also be used, examples include fatty acid salts such as the salts of oleic, ricinoleic, palmitic and stearic acids, coconut oil acid or hydrogenated coconut oil acid; acyl lactylates in which the acyl radical contains 8 to 20 carbon atoms. Use may also be made of slightly anionic surfactants, such as alkyl-D-galactosiduronic acids and their salts, and polyoxyalkylenated ($C_6$–$C_{24}$)alkyl ether carboxylic acids polyoxyalkylenated ($C_6$–$C_{24}$)alkyl aryl ether carboxylic acids, polyoxyalkylenated ($C_6$–$C_{24}$)alkyl amido ether carboxylic acids and their salts, in particular, those containing from 2 to 50 ethylene oxide groups, and mixtures thereof.

An anionic surfactant chosen from sodium, triethanolamine or ammonium ($C_{12}$–$C_{14}$)alkyl sulphates, sodium ($C_{12}$–$C_{14}$)alkyl ether sulphates oxyethylenated with 2.2 mol of ethylene oxide, sodium cocoyl isethionate and sodium alpha-($C_{14}$–$C_{16}$)olefin sulphonate is preferably used. Among the anionic surfactants, the ones preferably used according to the invention are alkyl sulphate salts and alkyl ether sulphate salts and mixtures thereof.

(ii) Amphoteric surfactant (s):

The amphoteric surfactants, whose nature is not a critical feature in the context of the present invention, can be, in particular (non-limiting list), aliphatic secondary or tertiary amine derivatives in which the aliphatic radical is a linear or branched chain containing 8 to 22 carbon atoms and containing at least one water-soluble anionic group (for example, carboxylate, sulphonate, sulphate, phosphate or phosphonate); examples also include ($C_8$–$C_{20}$)alkylbetaines, sulphobetaines, ($C_8$–$C_{20}$)alkylamido($C_1$–$C_6$)alkylbetaines or ($C_8$–$C_{20}$)alkylamido($C_1$–$C_6$)alkylsulphobetaines.

Among the amine derivatives, examples include the products sold under the name MIRANOL®, as described in U.S. Pat. Nos. 2,528,378 and 2,781,354, each incorporated herein by reference, and having the structures:

$$R_2\text{—CONHCH}_2\text{CH}_2\text{—N}(R_3)(R_4)(CH_2COO\text{—}) \quad (I)$$

in which: $R_2$ denotes an alkyl radical derived from an acid $R_9$—COOH present in hydrolysed coconut oil, a heptyl, nonyl or undecyl radical, wherein $R_9$ is a saturated or unsaturated, linear or branched ($C_5$–$C_{19}$)alkyl, $R_3$ denotes a beta-hydroxyethyl group and $R_4$ denotes a carboxymethyl group; and

$$R_{2'}\text{—CONHCH}_2\text{CH}_2\text{—N(B)(C)} \quad (II)$$

in which:

B represents —$CH_2CH_2OX'$, C represents —$(CH_2)_z$—$Y'$, with z=1 or 2,

X' denotes the —$CH_2CH_2$—COOH group or a hydrogen atom,

Y' denotes —COOH or the —$CH_2$—CHOH—$SO_3H$ radical, $R_{2'}$ denotes an alkyl radical of an acid $R_9$—COOH present in coconut oil or in hydrolysed linseed oil, an alkyl radical, in particular, a $C_7$, $C_9$, $C_{11}$ or $C_{13}$ alkyl radical, a $C_{17}$ alkyl radical and its iso form, or an unsaturated $C_{17}$ radical, wherein $R_9$ is a saturated or unsaturated, linear or branched ($C_5$–$C_{19}$)alkyl. These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid. By way of example, mention may be made of the cocoamphodiacetate sold under the trade name MIRANOL® C2M concentrate by the company Rhône-Poulenc. According to the present invention, preferred amphoteric surfactants include those belonging to the betaine group, such as alkylbetaines, especially the cocoylbetaine sold under the name "Dehyton AB 30" as an aqueous solution containing 30% AM by the company Henkel or alkylamidobetaines such as TEGOBETAINE® F50 sold by the company Goldschmidt.

The minimum amount of washing base is that just sufficient to give the final composition a satisfactory foaming and/or detergent power, and excessive amounts of washing base do not really afford any additional advantages. Thus, according to the invention, the washing base can represent from 4% to 50% by weight, preferably from 6% to 35% by weight and even more preferably from 8% to 25% by weight, relative to the total weight of the final composition.

As a guide, the detergent compositions according to the invention generally have the following compositions:

(i) anionic surfactant(s): from 1 to 30% by weight, preferably from 5 to 20% by weight, and more preferably from 5 to 12% by weight, relative to the total weight of the detergent composition;

(ii) amphoteric surfactant(s): from 0.15 to 20% by weight, preferably from 1.5 to 15% by weight, and more particularly from 3 to 15% by weight, relative to the total weight of the composition. The anionic surfactant/amphoteric surfactant weight ratio is less than or equal to 3:1, preferably ranging from 0.2:1 to 3:1, more particularly from 0.4:1 to 2.5:1.

B-Polyolefins

The compositions according to the invention comprise an oil of polyolefin type, i.e., a polyolefin oil, with a molecular weight of less than 450, preferably ranging from 150 to 350.

The polyolefins are preferably poly-α-olefins and, in particular:

of hydrogenated or non-hydrogenated polybutene type, and preferably hydrogenated or non-hydrogenated polyisobutene. Isobutylene oligomers with a molecular weight of less than 450 are preferably used. Examples of poly-α-olefins that can be used in the context of the present invention, include the products sold under the name Permethyl 99 A, 101 A and 102 A by the company Presperse Inc., or, alternatively, the products sold under the name Arlamol HD by the company ICI, of hydrogenated or non-hydrogenated polydecene type. Such products are sold, for example, under the names Ethylflo by the company Ethyl Corp., and Arlamol PAO by the company ICI.

The oil(s) of polyolefin type can be used in the compositions according to the invention in concentrations generally ranging from 0.5 to 15%, and preferably from 1 to 10%, by weight relative to the total weight of the composition, and even more particularly from 2 to 8% by weight.

C-Cationic Polymers

The cationic polymers that can be used in accordance with the present invention can be chosen from any of those already known per se as enhancing the cosmetic properties of hair treated with detergent compositions, namely, in particular, those described in European patent application EP-A-0,337,354 and in French patent applications FR-A-2, 270,846, 2,383,660, 2,598,611, 2,470,596 and 2,519,863, each incorporated herein by reference.

Even more generally, for the purposes of the present invention, the expression "cationic polymer" denotes any polymer containing cationic groups and/or groups that can be ionized into cationic groups. The cationic polymers that can be used according to the invention generally have a cationic charge density of greater than 0.2 meq./g. The preferred cationic polymers are chosen from those that contain units containing primary, secondary, tertiary and/or quaternary amine groups that can either form part of the main polymer chain or that can be carried by a lateral substituent that is directly attached thereto. The cationic polymers used generally have a number-average molecular mass ranging from 500 to $5\times10^6$ approximately, and preferably from $10^3$ to $3\times10^6$ approximately.

Among the cationic polymers, particular examples include polymers of quaternary polyammonium, polyamino amide and polyamine type. These are known products. The polymers of the quaternary polyammonium, polyaminoamide and polyamine type that can be used according to the present invention and that may be mentioned, in particular, are those described in French patents Nos. 2,505,348 or 2,542,997, each incorporated herein by reference. Among these polymers, examples include:

(1) Quaternized or non-quaternized vinylpyrrolidone/ dialkylaminoalkyl acrylate or methacrylate copolymers, such as the products sold under the name "Gafquat" by the company ISP such as, for example, Gafquat 734, 755 or HS100 or, alternatively, the product known as "Copolymer 937". These polymers are described in detail in French patents 2,077,143 and 2,393,573, each incorporated herein by reference.

(2) The cellulose ether derivatives containing quaternary ammonium groups, described in French patent 1,492,597, incorporated herein by reference, and, in particular, polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers or cellulose derivatives grafted with a water-soluble monomer of quaternary ammonium, and described, in particular, in U.S. Pat. No. 4,131,576, incorporated herein by reference, such as hydroxyalkylcelluloses, for instance hydroxymethyl-,hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are, more particularly, the products sold under the names "Celquat L 200" and "Celquat H 100" by the company National Starch.

(4) The cationic polysaccharides are described, more particularly, in U.S. Pat. Nos. 3,589,578 and 4,031,307, each incorporated by reference, such as guar gums containing cationic trialkylammonium groups. Guar gums modified with a salt (e.g. chloride) of 2,3-epoxypropyltrimethylammonium are used, for example.

Such products are sold, in particular, under the trade names Jaguar C13 S, Jaguar C 15, Jaguar C 17 or Jaguar C162 by the company Meyhall.

(5) Polymers comprising piperazinyl units and divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361, each incorporated herein by reference;

(6) Water-soluble polyamino amides prepared, in particular, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyidiamine, a bis-alkyl halide or, alternatively, with an oligomer resulting from the reaction of a difunctional compound that is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2,252,840 and 2,368,508, each incorporated herein by reference;

(7) The polyamino amide derivatives resulting from the condensation of polyalkylene polyamines with polycarboxylic acids followed by alkylation with difunctional agents. Mention may be made, for example, of adipic acid/ dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363, incorporated herein by reference. Among these derivatives, particular examples include the adipic acid/ dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described, in particular, in U.S. Pat. Nos. 3,227,615 and 2,961,347, each incorporated herein by reference. Polymers of this type are sold in particular under the name "Hercoseft 57" by the company Hercules Inc. or, alternatively, under the name "PD 170" or "Delsette 101" by the company Hercules in the case of the adipic acid/ epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (III) or (IV):

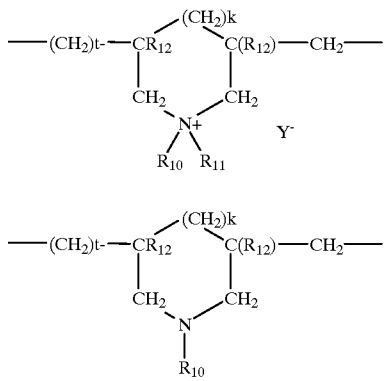 (III)

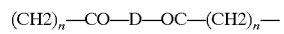 (IV)

in which formulae k and t are equal to 0 or 1, the sum k+t being equal to 1; $R_{12}$ denotes a hydrogen atom or a methyl radical; $R_{10}$ and $R_{11}$, which may be identical or different, denote an alkyl group having from 1 to 22 carbon atoms, a hydroxyalkyl group in which the alkyl group preferably has 1 to 5 carbon atoms, or a lower amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described, in particular, in French patent 2,080,759 and in its Certificate of Addition 2,190,406, incorporated herein by reference. Among the polymers defined above, mention may be made, more particularly, of the dimethyldiallylammonium chloride homopolymer sold under the name "Merquat 100" by the company Calgon and its homologues of low weight-average molecular mass.

(10) The quaternarydiammonium polymercontaining repeating units corresponding to the formula:

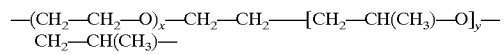 (V)

in which formula (V):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or, alternatively, $R_{13}$, $R_{14}$, $R_{15}$ and $R_{16}$, together or separately, constitute, with the nitrogen atoms to which they are attached, heterocycles optionally containing a second hetero atom other than nitrogen, or, alternatively, $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B_1$ represent polymethylene groups containing from 2 to 20 carbon atoms that may be linear or branched, saturated or unsaturated, and that may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH2)_n$—CO—D—OC—$(CH2)_n$— in which n is an integer ranging from 1 to 6, and D denotes:

a) a glycol residue of formula: —O—Z—O—, where Z denotes a linear or branched hydrocarbon radical or a group corresponding to one of the following formulae:

—$(CH_2—CH_2—O)_x$—$CH_2—CH_2$—$[CH_2—CH(CH_3)—O]_y$—$CH_2—CH(CH_3)$— where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon radical, or, alternatively, the divalent radical

—$CH_2$—$CH_2$—S—S—$CH_2$—$CH_2$—;

d) a ureylene group of formula: —NH—CO—NH—.

Preferably, $X^-$ is an anion, such as chloride or bromide.

These polymers generally have a number-average molecular mass ranging from 1000 to 100,000. Polymers of this type are described, in particular, in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, each incorporated herein by reference.

According to the invention, polymers chosen from the compounds of formula (V) in which $R_{13}$, $R_{14}$, $R_{15}$ and $R_{16}$ represent a methyl radical, $A_1$ represents the radical of formula —$(CH_2)_3$— and $B_1$ represents the radical of formula —$(CH_2)_6$— and $X^-$ represents the chloride anion, and the compound of formula (V) in which $R_{13}$ and $R_{14}$ represent an ethyl radical, $R_{15}$ and $R_{16}$ represent a methyl radical, $A_1$ and $B_1$ represent the radical of formula —$(CH_2)_3$— and $X^-$ represents the bromide anion, can be used more particularly.

(11) Quaternary polyammonium polymers comprising units of formula (VI):

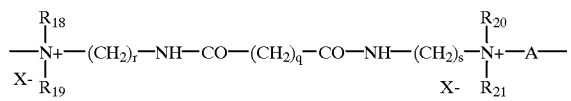 (VI)

in which formula:

$R_{18}$, $R_{19}$, $R_{20}$ and $R_{21}$, which may be identical or different, represent a hydrogen atom or a methyl, ethyl, propyl, b-hydroxyethyl, b-hydroxypropyl or —CH$_2$CH$_2$(OCH$_2$CH$_2$)$_p$OH radical, where p is equal to 0 or to an integer ranging from 1 to 6, with the proviso that R$_{18}$, R$_{19}$, R$_{20}$ and R$_{21}$ do not simultaneously represent a hydrogen atom, r and s, which may be identical or different, are integers ranging from 1 to 6, q is equal to 0 or to an integer ranging from 1 to 34, X denotes a halogen atom, A denotes a dihalide radical or preferably represents —CH$_2$—CH$_2$—O—CH$_2$—CH$_2$—.

Such compounds are described, in particular, in European patent application EP-A-122,324, incorporated herein by reference. Among these products, mention may be made, for example, of "Mirapol A 15", "Mirapol AD1", "Mirapol AZ1" and "Mirapol 175" sold by the company Miranol.

(12) Homopolymers or copolymers derived from acrylic or methacrylic acids and containing units:

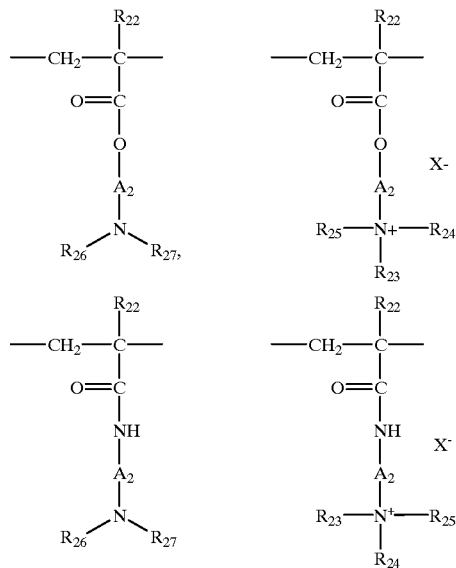

in which the groups R$_{22}$ independently denote H or CH$_3$, the groups A$_2$ independently denote a linear or branched alkyl group of 1 to 6 carbon atoms or a hydroxyalkyl group of 1 to 4 carbon atoms, the groups R$_{23}$, R$_{24}$ and R$_{25}$, which may be identical or different, independently denote an alkyl group of 1 to 18 carbon atoms or a benzyl radical, the groups R$_{26}$ and R$_{27}$ represent a hydrogen atom or an alkyl group of 1 to 6 carbon atoms, X$^-$ denotes an anion, for example methosulphate or halide, such as chloride or bromide.

The comonomer(s) that can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(13) Quaternary polymers of vinylpyrrolidone and of vinylimidazole, such as, for example, the products sold under the names Luviquat FC 905, FC 550 and FC 370 by the company BASF.

(14) Polyamines such as Polyquart H sold by Henkel under the reference name "Polyethylene glycol (15) tallow polyamine" in the CTFA dictionary.

(15) Polymers of methacryloyloxy(C$_1$-C$_4$)alkyltri(C$_1$-C$_4$)alkylammonium salts such as the polymers obtained by homopolymerization of dimethylaminoethyl methacrylate quaternized with methyl chloride, or by copolymerization of acrylamicle with dimethylaminoethyl methacrylate quaternized with methyl chloride, the homo- or copolymerization being followed by crosslinking with a compound containing olefinic unsaturation, in particular, methylenebisacrylamide. A crosslinked acrylamide/methacryloyloxyethyltrimethylammonium chloride copolymer (20/80 by weight) in the form of a dispersion containing 50% by weight of the copolymer in mineral oil can be used more particularly. This dispersion is sold under the name "SALCARE® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "SALCARE® SC 95 and SC 96" by the company Allied Colloids.

Other cationic polymers that can be used in the context of the invention are polyalkyleneimines, in particular, polyethyleneimines, polymers containing vinylpyridine or vinylpyridinium units, condensates of polyamines and of epichlorohydrin, quaternary polyureylenes and chitin derivatives.

Among all the cationic polymers that can be used in the context of the present invention, it is preferred to use cyclopolymers, in particular, homopolymers of a diallyidimethylammonium salt and copolymers of a diallyldimethylammonium salt and of acrylamide, in particular, the chlorides, sold under the names "Merquat 100", "Merquat 550" and "Merquat S" by the company Calgon, optionally crosslinked homopolymers and copolymers of a (meth) acryloyloxyethyltrimethylammonium salt, sold by the company Allied Colloids as a 50% solution in mineral oil, under the trade names Salcare SC92 (crosslinkedl copolymer of methacryloyloxyethyltrimethylammonium chloride and of acrylamide) and Salcare SC95 (crosslinked homopolymer of methacryloyloxyethyltrimethylammonium chloride), copolymers of vinylpyrrolidone and of a vinylimidazoline salt, such as the products sold by BASF under the names Luviquat FC 370, Luviquat FC 550, Luviquat FC 905 and Luviquat HM-552.

It is also possible to use the polymers that comprise repeating units corresponding to the formula:

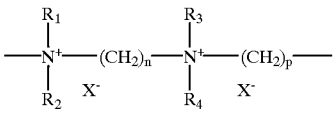

(VII)

in which R$_1$, R$_2$, R$_3$ and R$_4$, which may be identical or different, denote an alkyl or hydroxyalkyl radical containing from 1 to 4 carbon atoms approximately, n and p are integers ranging from 2 to 20 approximately and X$^-$ is an anion derived from an inorganic or organic acid. One compound of formula (VII) that is particularly preferred is the one for which R$_1$, R$_2$, R$_3$ and R$_4$ represent a methyl radical and n=3, p=6 and X=CI, referred to as hexadimethrine chloride according to the INCI (CTFA) nomenclature.

According to the invention, the cationic polymer(s) can represent from 0.05% to 10% by weight, preferably from 0.1% to 5% by weight and even more preferably from 0.25% to 3% by weight, relative to the total weight of the final composition.

D-Water-Soluble Salts and Alcohols

The water-soluble salts according to the invention are preferably mono- or divalent metal salts of an inorganic or organic acid. Examples include sodium chloride, potassium chloride, calcium chloride, magnesium sulphate, sodium citrate and sodium salts of phosphoric acid. Preferably, monovalent metal salts are used. Sodium chloride is particularly preferred. The water-soluble salts are generally present in concentrations ranging from 0.1 to 10% by weight, and preferably from 0.5 to 5% by weight, relative to the total weight of the composition. The mono- or polyhydroxylated water-soluble alcohols are, in particular, $C_1$–$C_6$ lower alcohols, such as ethanol, isopropanol, tert-butanol, n-butanol, polyols such as alkylene glycols, for instance propylene glycol, glycerol and polyalkylene glycols; glycol ethers. The water-soluble alcohol(s) can be used in concentrations generally ranging from 0.1 to 20% by weight, and more particularly from 0.2 to 10% by weight, relative to the total weight of the composition.

The detergent compositions according to the invention have a final pH generally ranging from 3 to 8. Preferably, this pH ranges from 4 to 6.5. Adjustment of the pH to the desired value can be carried out conventionally by adding a base (organic or inorganic) to the composition, for example sodium hydroxide, aqueous ammonia or a primary, secondary or tertiary (poly)amine such as monoethanolamine, diethanolamine, triethanolamine, isopropanolamine or 1,3-propanediamine, or, alternatively, by adding an inorganic or organic acid, preferably citric acid or hydrochloric acid.

The cosmetically acceptable aqueous medium can comprise solely water or a mixture of water and a cosmetically acceptable solvent.

The compositions according to the invention can contain, in addition to the combination defined above, viscosity modifiers, such as electrolytes, or thickeners. Particular examples include sodium xylenesulphonate, scleroglucans, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked polyacrylic acids and crosslinked acrylic acid/ $C_{10}$–$C_{30}$ alkyl acrylate copolymers. These viscosity modifiers are used in the compositions according to the invention in proportions that can range up to 10% by weight relative to the total weight of the composition.

The compositions according to the invention can also contain up to 5% of pearlescent agents or opacifiers that are well known in the state of the art, such as, for example, fatty alcohols, sodium or magnesium palmitate, sodium or magnesium stearate or hydroxystearate, fatty alcohols, acyl derivatives containing a fatty chain, such as monostearates or distearates of ethylene glycol or of polyethylene glycol, ethers containing fatty chains, such as, for example, distearyl ether or 1-(hexadecyloxy)-2-octadecanol.

The compositions according to the invention can also optionally contain other agents that have the effect of improving the cosmetic properties of the hair or the skin without, however, adversely affecting the stability of the compositions. In this respect, examples include cationic surfactants, anionic or nonionic or amphoteric polymers, proteins, protein hydrolysates, ceramides, pseudoceramides, fatty acids containing linear or branched $C_{16}$–$C_{40}$ chains, such as 18-methyleicosanoic acid, hydroxy acids, vitamins, panthenol, volatile or non-volatile silicones, that may be soluble or insoluble in the medium, UV screening agents, moisturizers, antidandruff or anti-seborrhoeic agents, free-radical scavengers and mixtures thereof.

The compositions according to the invention can also contain foam synergists such as $C_{10}$–$C_{18}$ 1,2-alkanediols or fatty alkanolamides derived from mono- or diethanolamine.

Needless to say, a person skilled in the art will take care to select this or these additional compound(s) and/or the amounts thereof such that the stability of the compositions and the cosmetic properties intrinsically associated with the compositions according to the invention are not, or are not substantially, adversely affected by the addition(s) envisaged.

The transparency can be measured by means of the turbidity with a Hach model 2100 P turbidimeter at 25° C. (the device is calibrated with formazine). The turbidity of the compositions according to the invention (in the absence of additional insoluble compounds) then generally ranges from 0.05 to 50 NTU and preferably less than 25 NTU. When the oil is in the form of globules, the size of these oil globules is preferably less than 5 nanometers.

The foaming power of the compositions according to the invention, characterized by a foam height, is generally greater than 75 mm; preferably greater than 100 mm, measured according to the modified Ross-Miles method (NF T 73-404/ISO696). The modifications to the method are as follows:

The measurement is carried out at a temperature of 22° C. with osmosed water. The concentration of the solution is 2 g/l. The height of the drop is 1 m. The amount of composition which drops is 200 ml. These 200 ml of composition fall into a measuring cylinder with a diameter of 50 mm and containing 50 ml of the test composition. The measurement is made 5 minutes after stopping the flow of the composition.

These compositions can be in the form of more or less thickened liquids, creams or gels and they are mainly suitable for washing and caring for keratin substances, in particular, the hair and the skin, and, even more particularly, the hair.

A subject of the invention is also a process for washing and conditioning keratin fibers such as, in particular, the hair, which comprises applying an effective amount of a composition as defined above to the wet substances and then rinsing with water, after optionally leaving the composition to stand on the substances for a period of time. The compositions according to the invention are preferably used as shampoos for washing and conditioning the hair and, in this case, they are applied to wet hair in amounts that are effective for washing it, and the lather generated by massaging or friction with the hands is then removed, after the shampoo has optionally been left to stand on the hair for a period of time, by rinsing with water, it being possible for the operation to be repeated one or more times. The compositions according to the invention can also be used as shower gels for washing and conditioning the hair and/or the skin, in which case they are applied to wet skin and/or hair and are rinsed off after application.

The present invention is further illustrated by the following examples which are designed to teach those of ordinary skill in the art how to practice the invention. The following examples are merely illustrative of the invention and should not be construed as limiting the invention as claimed.

EXAMPLE 1

Two shampoo compositions, one according to the invention (composition A) and the other comparative (composition B), were prepared:

|  | B comparative | A invention |
|---|---|---|
| Sodium lauryl ether sulphate (70/30 C12/C14) containing 2.2 mol of ethylene oxide, as an aqueous solution containing 70% AM | 17.5 g AM | 7.5 g AM |
| Cocoylbetaine (Dehyton AB 30) | 2.5 g AM | 12.5 g AM |
| 2,2,4,4,6,6,8-Heptamethylnonane (isohexadecane from Bayer) | 2 g | 2 g |
| Diallyldimethylammonium chloride homopolymer as an aqueous solution containing 40% AM (Merquat 100 from Calgon) | 0.4 g AM | 0.4 g AM |
| NaCl | 4 g | 4 g |
| Fragrance, preserving agent | qs | qs |
| Hydrochloric acid qs pH | 6 | 6 |
| Demineralized water qs | 100 g | 100 g |

Composition A according to the invention (anionic surfactant/amphoteric surfactant=0.6) was transparent. Turbidity=31.4 NTU. Composition B (anionic surfactant/amphoteric surfactant=7) was not transparent. Turbidity= >900 NTU (The transparency was evaluated by turbidimetry in NTU units (Nephelometric turbidity units)).

A shampooing operation was carried out by applying about 1 g of composition A to locks of pre-dampened sensitized hair (2.5 g). The shampoo was worked into a lather, left to stand on the hair for 10 min and then rinsed thoroughly with water. The locks were dried. The process was performed according to the same procedure as above with the comparative composition B.

A panel of experts evaluated the appearance of the hair dried for 10 minutes at 60° C. All the experts indicated that the hair treated with composition A according to the invention disentangled more easily, was softer and smoother than the hair treated with composition B.

EXAMPLE 2

Two shampoo compositions were prepared, one according to the invention (composition A) and the other comparative (composition B):

|  | B comparative | A invention |
|---|---|---|
| Polyoxyethylenated lauryl ether carboxylic acid as an aqueous solution containing 90% AM (Akypo RLM 45 CA from KAO) | 8 g AM | 8 g AM |
| Sodium cocoamphocarboxyglycinate as an aqueous solution containing 38% AM (Miranol C2M Conc. from Rhodia Chimie) | 4 g AM | 4 g AM |
| 2,2,4,4,6,6,8-Heptamethylnonane (isohexadecane from Bayer) | 1 g | 1 g |
| Diallyldimethylammonium chloride homopolymer as an aqueous solution containing 40% AM (Merquat 100 from Calgon) | — | 0.4 g AM |
| NaCl | — | 4 g |
| Fragrance, preserving agent | qs | qs |
| Hydrochloric acid qs pH | 6 | 6 |
| Demineralized water qs | 100 g | 100 g |

A shampooing operation was carried out by applying about 1 g of composition A to locks of pre-dampened sensitized hair (2.5 g). The shampoo was worked into a lather, left to stand on the hair for 10 min and then rinsed thoroughly with water. The locks were dried. The process was performed according to the same procedure as above with the comparative composition B.

A panel of experts evaluated the appearance of the hair dried for 10 minutes at 60° C. All the experts indicated that the hair treated with composition A according to the invention disentangled more easily, was softer and smoother than the hair treated with composition B.

EXAMPLE 3

Three shampoo compositions were prepared, two according to the invention (compositions A and C) and the other comparative (composition B):

|  | B comparative | A invention | C invention |
|---|---|---|---|
| Ammonium lauryl ether sulphate containing 3 mol of ethylene oxide, as an aqueous solution containing 70% AM (AM = active material) | 10 g AM | 8.33 g AM | 6.25 g AM |
| Cocoamidopropylbetaine | 3 g AM | 5 g AM | 7.5 g AM |
| Sodium lauryl sulfosuccinate | 2 g AM | 1.67 g AM | 1.25 g AM |
| Isoeicosane (Permethyl 102 A) | 0.5 g | 0.5 g | 0.5 g |
| Copolymer of diallyldimethyl-ammonium chloride and of acrylamide as an aqueous solution containing 8% AM (Merquat 550 from Calgon) | 0.2 g AM | 0.2 g AM | 0.2 g AM |
| NaCl | — | 2 g | 2 g |
| Fragrance, preserving agent | qs | qs | qs |
| Hydrochloric acid qs pH | 6 | 6 | 6 |
| Demineralized water qs | 100 g | 100 g | 100 g |

Composition A according to the invention (anionic surfactant/amphoteric surfactant=2) was transparent. Turbidity=6.06 NTU. Composition B (anionic surfactant/amphoteric surfactant=4) was not transparent. Turbidity= 110 NTU.

A shampooing operation was carried out by applying about 1 g of composition A to locks of pre-dampened sensitized hair (2.5 g). The shampoo was worked into a lather, left to stand on the hair for 10 min and then rinsed thoroughly with water. The locks were dried. The process was performed according to the same procedure as above with the comparative composition B, as was composition C of the present invention.

A panel of experts evaluated the appearance of the hair dried for 10 minutes at 60° C. 90% of the experts indicated that the hair treated with composition A according to the invention disentangled more easily, was softer and smoother than the hair treated with composition B. Similarly, 90% of the experts indicated that the hair treated with composition C according to the invention disentangled more easily, was softer and smoother than the hair treated with composition B.

The foregoing written description relates to various embodiments of the present invention. Numerous changes and modifications may be made therein without departing from the spirit and scope of the invention as defined in the following claims.

What is claimed is:

1. A detergent and conditioning cosmetic composition comprising:

(A) a washing base comprising at least one anionic surfactant, and at least one amphoteric surfactant, (B) at least one polyolefin oil having a molecular weight of less than 450, (C) at least one cationic polymer, and (D) at least one water-soluble salt, at least one mono- or polyhydroxylated water-soluble alcohol, or mixtures thereof, wherein the anionic surfactant/amphoteric surfactant weight ratio is less than or equal to 3.

2. A composition according to claim 1, wherein said composition is in a cosmetically acceptable aqueous medium.

3. A composition according to claim 1, wherein said washing base is present in an amount ranging from 4% to 50% by weight relative to the total weight of the composition.

4. A composition according to claim 3, wherein said washing base is present in an amount ranging from 6% to 35% by weight relative to the total weight of the composition.

5. A composition according to claim 4, wherein said washing base is present in an amount ranging from 8% to 25% by weight relative to the total weight of the composition.

6. A composition according to claim 1, wherein said at least one anionic surfactant is present in an amount ranging from 1 to 30% by weight relative to the total weight of the composition.

7. A composition according to claim 6, wherein said at least one anionic surfactant is present in an amount ranging from 5 to 20% by weight relative to the total weight of the composition.

8. A composition according to claim 1, wherein said at least one amphoteric surfactant is present in an amount ranging from 0.15 to 20% by weight relative to the total weight of the composition.

9. A composition according to claim 8, wherein said at least one amphoteric surfactant is present in an amount ranging from 1.5 to 15% by weight relative to the total weight of the composition.

10. A composition according to claim 1, wherein said anionic surfactant/amphoteric surfactant weight ratio ranges from 0.2:1 to 3:1.

11. A composition according to claim 10, wherein said anionic surfactant/amphoteric surfactant weight ratio ranges from 0.4:1 to 2.5:1.

12. A composition according to claim 1, wherein said at least one polyolefin oil has a molecular weight ranging from 150 to 350.

13. A composition according to claim 1, wherein said at least one polyolefin oil is a poly-α-olefin oil.

14. A composition according to claim 13, wherein said at least one poly-α-olefin oil is chosen from oils:

of hydrogenated or non-hydrogenated polybutene, and of hydrogenated or non-hydrogenated polydecene.

15. A composition according to claim 14, wherein said oils of hydrogenated or non-hydrogenated polybutene are chosen from hydrogenated and non-hydrogenated polyisobutene.

16. A composition according to claim 1, wherein said at least one polyolefin oil is present in an amount ranging from 0.5 to 15% relative to the total weight of the composition.

17. A composition according to claim 16, wherein said at least one polyolefin oil is present in an amount ranging from 1 to 10% relative to the total weight of the composition.

18. A composition according to claim 1, wherein said at least one cationic polymer is chosen from:

(1) quaternized or non-quaternized vinylpyrrolidone/dialkylaminoalkyl acrylate or methacrylate copolymers;

(2) cellulose ether derivatives containing quaternary ammonium groups;

(3) cationic cellulose derivatives;

(4) polysaccharides;

(5) polymers comprising piperazinyl units and divalent alkylene or hydroxyalkylene radicals containing straight or branched chains, optionally interrupted by oxygen, sulphur or nitrogen atoms or by aromatic or heterocyclic rings, and/or oxidation and/or quaternization products thereof;

(6) water-soluble polyamino amides;

(7) polyamino amide derivatives resulting from the condensation of polyalkylene polyamines with polycarboxylic acids followed by alkylation with difunctional agents;

(8) polymers obtained by reacting a polyalkylene polyamine containing two primary amine groups and at least one secondary amine group with a dicarboxylic acid chosen from diglycolic acid and saturated aliphatic dicarboxylic acids having from 3 to 8 carbon atoms; wherein the molar ratio between said polyalkylene polyamine and said dicarboxylic acid ranges from 0.8:1 to 1.4:1; and wherein a polyamino amide resulting therefrom is reacted with epichlorohydrin in a molar ratio of epichlorohydrin relative to the secondary amine group of the polyamino amide ranging from 0.5:1 to 1.8:1;

(9) cyclopolymers of methyldiallylamine or of dimethyidiallylammonium;

(10) a quaternary diammonium polymer containing repeating units corresponding to the formula:

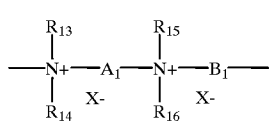

(V)

in which:

$R_{13}$, $R_{14}$, $R_{15}$ and $R_{16}$ are identical or different, and are chosen from aliphatic, alicyclic and arylaliphatic radicals containing from 1 to 20 carbon atoms and lower hydroxyalkylaliphatic radicals; or $R_{13}$, $R_{14}$, $R_{15}$ and $R_{16}$, together or separately, constitute, with the nitrogen atoms to which they are attached, heterocycles optionally containing a second hetero atom other than nitrogen; or $R_{13}$, $R_{14}$, $R_{15}$ and $R_{16}$ are identical or different, and are chosen from a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B_1$ are chosen from polymethylene groups containing from 2 to 20 carbon atoms which are linear or branched, saturated or unsaturated, and which optionally contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups; and $X^-$ is an anion derived from an inorganic or organic acid;

$A_1$, $R_{13}$ and $R_{15}$ can form, with the two nitrogen atoms to which they are attached, a piperazine ring; if $A_1$ is a linear or branched, saturated or unsaturated alkylene or hydroxyalkylene radical, then $B_1$ can also be a group

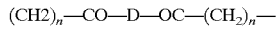

in which n is an integer ranging from 1 to 6, and D is chosen from:
a) a glycol residue of formula: $-O-Z-O-$, wherein Z is chosen from a linear or branched hydrocarbon radical and a group corresponding to the following formulae:

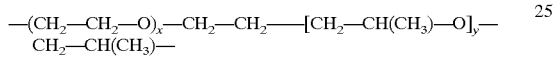

where x and y are chosen from an integer ranging from 1 to 4, representing a defined and unique degree of polymerization or any number ranging from 1 to 4 representing an average degree of polymerization;
b) a bis-secondary diamine residue;
c) a bis-primary diamine residue of formula: $-NH-Y-NH-$, wherein Y is chosen from a linear or branched hydrocarbon radical, and the divalent radical

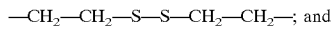

d) a ureylene group of formula: $-NH-CO-NH-$;

(11) quaternary polyammonium polymers comprising units of formula (VI):

(VI)

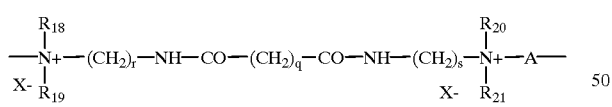

in which:
$R_{18}$, $R_{19}$, $R_{20}$ and $R_{21}$ are identical or different, and are chosen from a hydrogen atom or a methyl, ethyl, propyl, β-hydroxyethyl, β-hydroxypropyl and $-CH_2CH_2(OCH_2CH_2)_pOH$ radical,
wherein p is equal to 0 or to an integer ranging from 1 to 6, with the proviso that $R_{18}$, $R_{19}$, $R_{20}$ and $R_{21}$ do not simultaneously represent a hydrogen atom,
r and s are identical or different, and are chosen from integers ranging from 1 to 6,
q is equal to 0 or to an integer ranging from 1 to 34,
X is a halogen atom, and
A is a dihalide radical or $-CH_2-CH_2-O-CH_2-CH_2-$;

(12) homopolymers or copolymers derived from acrylic or methacrylic acids and containing units chosen from:

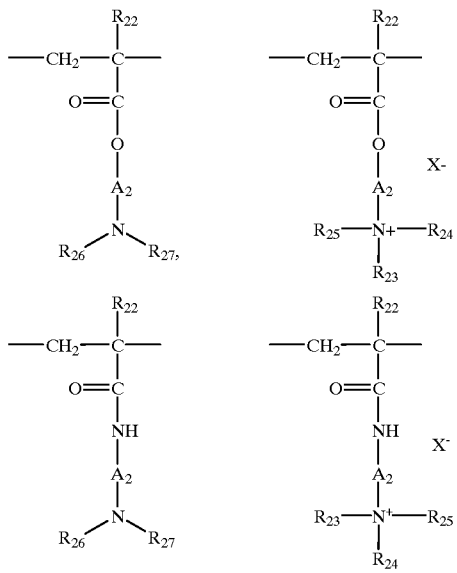

in which said groups $R_{22}$ independently are chosen from H and $CH_3$,
said groups $A_2$ independently are chosen from a linear or branched alkyl group of 1 to 6 carbon atoms and a hydroxyalkyl group of 1 to 4 carbon atoms,
said groups $R_{23}$, $R_{24}$ and $R_{25}$ are identical or different, and independently are chosen from an alkyl group of 1 to 18 carbon atoms and a benzyl radical,
said groups $R_{26}$ and $R_{27}$ are identical or different, and are chosen from a hydrogen atom and an alkyl group of 1 to 6 carbon atoms, and
$X^-$ is an anion;

(13) quaternary polymers of vinylpyrrolidone and of vinylimidazole;

(14) polyamines;

(15) crosslinked polymers of methacryloyloxy($C_1$–$C_4$)alkyltri($C_1$–$C_4$)alkylammonium salts; and

(16) polyalkyleneimines, polymers containing vinylpyridine or vinylpyridinium units, condensates of polyamines and of epichlorohydrin, quaternary polyureylenes and chitin derivatives.

19. A composition according to claim 18, wherein:
said cationic cellulose derivatives are chosen from cellulose copolymers and cellulose derivatives grafted with a water-soluble monomer of quaternary ammonium;
said polysaccharides are chosen from guar gums containing cationic trialkylammonium groups;
said water-soluble polyamino amides are chosen from water-soluble polyamino amides prepared by polycondensation of an acidic compound with a polyamine;
said cyclopolymers of methyldiallylamine or of dimethyldiallylammonium are chosen from homopolymers or copolymers containing, as main constituent of the chain, units corresponding to formula (III) and (IV):

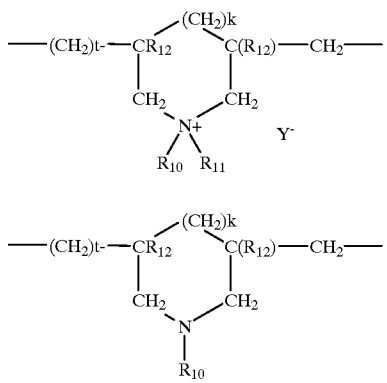

in which formulae k and t are equal to 0 or 1, and the sum k+t is equal to 1;

$R_{12}$ is chosen from a hydrogen atom and a methyl radical;

$R_{10}$ and $R_{11}$, which are the same or different, and are chosen from an alkyl group having from 1 to 22 carbon atoms, a hydroxyalkyl group, and a lower amidoalkyl group, or $R_{10}$ and $R_{11}$ are, together with the nitrogen atom to which they are attached, heterocyclic groups, and Y⁻ is an anion;

said D, in said quaternary diammonium polymer containing repeating units corresponding to said formula (V), is a piperazine derivative;

said X⁻, in said homopolymers or copolymers derived from acrylic or methacrylic acid, is chosen from methosulphate and a halide;

said crosslinked polymers of methacryloyloxy($C_1$–$C_4$) alkyltri($C_1$–$C_4$)alkylammonium salts are chosen from polymers obtained by homopolymerization of dimethylaminoethyl methacrylate quaternized with methyl chloride, and by copolymerization of acrylamide with dimethylaminoethyl methacrylate quaternized with methyl chloride, the homo- or copolymerization being followed by crosslinking with a compound containing olefinic unsaturation;

said polyalkyleneimines are chosen from polyethyleneimines.

20. A composition according to claim 19, wherein:

said water-soluble polyamino amides are crosslinked with an epihalohydrin, a diepoxide, a dianhydride, an unsaturated dianhydride, a bis-unsaturated derivative, a bis-halohydrin, a bis-azetidinium, a bis-haloacyidiamine, a bis-alkyl halide or with an oligomer resulting from the reaction of a difunctional compound which is reactive with a bis-halohydrin, a bis-azetidinium, a bis-haloacyidiamine, a bis-alkyl halide, an epihalohydrin, a diepoxide or a bis-unsaturated derivative;

in said cyclopolymers of methyldiallylamine or dimethyldiallylammonium, said $R_{10}$ and $R_{11}$, independently of each other, are a hydroxyalkyl group, wherein said alkyl as from 1 to 5 carbon atoms, or $R_{10}$ and $R_{11}$ together with the nitrogen atom to which they are attached form pieridyl or morpholinyl; and/or Y— is chosen from bromide, chloride, acetate, borate, citrate, tartrate, bisulphate, bisulphite, sulphate and phosphate;

in said homopolymers or copolymers derived from acrylic or methacrylic acids, said X⁻ is chosen from chloride and bromide;

in said crosslinked polymers of methacryloyloxy($C_1$–$C_4$) alkyltri($C_1$–$C_4$)alkylammonium salts, said compound containing olefinic unsaturation is methylenebisacrylamide.

21. A composition according to claim 20, wherein in said water-soluble polyamino amides, said crosslinking agent is present in an amount ranging from 0.025 to 0.35 mol per amine group of the polyamino amide.

22. A composition according to claim 20, wherein said water-soluble polyamino amides are optionally alkylated or, if they contain at least one tertiary amine functions, they are optionally quaternized.

23. A composition according to claim 18, wherein said at least one cationic polymer is chosen from:

cyclopolymers, optionally crosslinked homopolymers and copolymers of a (meth)acryloyloxyethyltrimethylammonium salt, copolymers of vinylpyrrolidone and of a vinylimidazole salt, and polymers comprising repeating units corresponding to the formula:

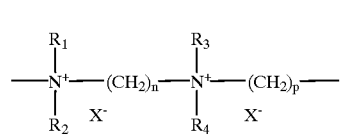

in which $R_1$, $R_2$, $R_3$ and $R_4$ are identical or different, and are chosen from an alkyl and a hydroxyalkyl radical containing from about 1 to about 4 carbon atoms, n and p are integers ranging from about 2 to about 20, and X⁻ is an anion derived from an inorganic or organic acid.

24. A composition according to claim 23, wherein said cyclopolymers are chosen from homopolymers of a diallyldimethylammonium salt and copolymers of a diallyidimethylammonium salt and of acrylamide.

25. A composition according to claim 1, wherein said at least one cationic polymer is present in an amount ranging from 0.05 to 10% by weight relative to the total weight of the composition.

26. A composition according to claim 25, wherein said at least one cationic polymer is present in an amount ranging from 0.1 to 5% by weight relative to the total weight of the composition.

27. A composition according to claim 26, wherein said at least one cationic polymer is present in an amount ranging from 0.25 to 3% by weight relative to the total weight of the composition.

28. A composition according to claim 1, wherein said at least one water-soluble salt is a mono- or divalent metal salt of an inorganic or organic acid.

29. A composition according to claim 28, wherein said at least one water-soluble salt is chosen from sodium chloride, potassium chloride, calcium chloride, magnesium sulphate, sodium citrate and sodium salts of phosphoric acid.

30. A composition according to claim 1, wherein said at least one water-soluble salt is present in an amount ranging from 0.1 to 10% by weight relative to the total weight of the composition.

31. A composition according to claim 30, wherein said at least one water-soluble salt is present in an amount ranging from 0.5 to 5% by weight relative to the total weight of the composition.

32. A composition according to claim 1, wherein said at least one mono- or polyhydroxylated water-soluble alcohol is chosen from $C_1$–$C_6$ lower alcohols, polyols, and glycol ethers.

33. A composition according to claim 32, wherein said at least one mono- or polyhydroxylated water-soluble alcohol is chosen from ethanol, isopropanol, tert-butanol, n-butanol, and alkylene glycols.

34. A composition according to claim 33, wherein said at least one mono- or polyhydroxylated water-soluble alcohol is chosen from propylene glycol, glycerol, and polyalkylene glycols.

35. A composition according to claim 1, wherein said at least one mono- or polyhydroxylated water-soluble alcohol is present in an amount ranging from 0.1 to 20% by weight relative to the total weight of the composition.

36. A composition according to claim 35, wherein said at least one mono- or polyhydroxylated water-soluble alcohol is present in an amount ranging from 0.2 to 10% by weight relative to the total weight of the composition.

37. A composition according to claim 1, further comprising at least one adjuvant chosen from cationic surfactants, anionic polymers, nonionic polymers, amphoteric polymers, proteins, protein hydrolysates, ceramides, pseudoceramides, a fatty acid containing linear or branched $C_{16}$–$C_{40}$ chains, hydroxy acids, vitamins, panthenol, volatile and non-volatile silicones, which are soluble or insoluble in the medium, UV screening agents, moisturizers, antidandruff or antiseborrhoeic agents, free-radical scavengers.

38. A composition according to claim 37, wherein said fatty acid containing linear or branched $C_{16}$–$C_{40}$ chains is 18-methyleicosanoic acid.

39. A method of cleansing a keratin substance comprising applying an effective amount of a composition to said keratin substance, wherein said composition comprises (A) a washing base comprising at least one anionic surfactant, and at least one amphoteric surfactant, (B) at least one polyolefin oil having a molecular weight of less than 450, (C) at least one cationic polymer, and (D) at least one water-soluble salt, at least one mono- or polyhydroxylated water-soluble alcohol, or mixtures thereof, wherein the anionic surfactant/amphoteric surfactant weight ratio is less than or equal to 3:1.

40. A method of removing make-up from a keratin substance comprising applying an effective amount of a composition to said keratin substance, wherein said composition comprises (A) a washing base comprising at least one anionic surfactant, and at least one amphoteric surfactant, (B) at least one polyolefin oil having a molecular weight of less than 450, (C) at least one cationic polymer, and (D) at least one water-soluble salt, at least one mono- or polyhydroxylated water-soluble alcohol, or mixtures thereof, wherein the anionic surfactant/amphoteric surfactant weight ratio is less than or equal to 3:1.

41. A method of conditioning a keratin substance comprising applying an effective amount of a composition to said keratin substance, wherein said composition comprises (A) a washing base comprising at least one anionic surfactant, and at least one amphoteric surfactant, (B) at least one polyolefin oil having a molecular weight of less than 450, (C) at least one cationic polymer, and (D) at least one water-soluble salt, at least one mono- or polyhydroxylated water-soluble alcohol, or mixtures thereof, wherein the anionic surfactant/amphoteric surfactant weight ratio is less than or equal to 3:1.

42. A process for washing and conditioning a keratin substance, comprising:

applying an effective amount of a composition to said keratin substance, wherein said composition comprises (A) a washing base comprising at least one anionic surfactant, and at least one amphoteric surfactant, (B) at least one polyolefin oil having a molecular weight of less than 450, (C) at least one cationic polymer, and (D) at least one water-soluble salt, at least one mono- or polyhydroxylated water-soluble alcohol, or mixtures thereof, wherein the anionic surfactant/ amphoteric surfactant weight ratio is less than or equal to 3:1, and then rinsing said keratin substance with water, after optionally leaving said composition to stand on said keratin substance for a period of time.

43. A process according to claim 42, wherein said keratin substance is hair.

44. A process according to claim 42, further comprising wetting said keratin substance before said applying said composition.

* * * * *

UNITED STATES PATENT AND TRADEMARK OFFICE
CERTIFICATE OF CORRECTION

PATENT NO. : 6,338,842 B1
DATED : January 15, 2002
INVENTOR(S) : Serge Restle et al.

It is certified that error appears in the above-identified patent and that said Letters Patent is hereby corrected as shown below:

<u>Title page,</u>
Item [74], *Attorney, Agent or Firm*,
Line 2, "L.L.P" should read -- L.L.P. --.

<u>Column 16,</u>
Lines 35-36, "dimethyidiallylammonium" should read -- dimethyldiallylammonium --.

<u>Column 19,</u>
Line 51, "bis-haloacyidiamine" should read -- bis-haloacyldiamine --.
Lines 54-55, "bis-haloacyidiamine" should read -- bis-haloacyldiamine --.

<u>Column 20,</u>
Lines 39-40, "diallyidimethylammonium" should read -- diallyldimethylammonium --.

Signed and Sealed this

Twenty-third Day of April, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.     : 6,338,842 B1
DATED          : January 15, 2002
INVENTOR(S)    : Serge Restle et al.

It is certified that error appears in the above-identified patent and that said Letters Patent is hereby corrected as shown below:

<u>Title page,</u>
Item [56], U.S. PATENT DOCUMENTS, the following references should also be cited as follows:
--      5,324,507 A    06/1994     Dubief et al. ............... 424/70
        5,786,310 A    07/1998     Dubief et al. ............... 510/122 --

Item [56], FOREIGN PATENT DOCUMENTS, the following references should also be cited as follows:
--     EP        0 500 423       08/1992
       WO      WO 93/08787     05/1993
       WO      WO 94/06409     03/1994
       WO      WO 95/22311     08/1995
       WO      WO 97/09031     03/1997
       WO      WO 97/14396     04/1997
       WO      WO 97/35545     10/1997
       WO      WO 97/35546     10/1997
       WO      WO 98/18443     05/1998       --

Signed and Sealed this

Twenty-first Day of January, 2003

JAMES E. ROGAN
*Director of the United States Patent and Trademark Office*